United States Patent [19]

Stahel

[11] Patent Number: 5,614,373
[45] Date of Patent: Mar. 25, 1997

[54] TUMOR-SPECIFIC ANTIBODIES AND ANTIGEN

[75] Inventor: Rolf Stahel, Forch, Switzerland

[73] Assignee: Merck Patent Gesellschaft Mit Beschrankter Haftung, Darmstadt, Germany

[21] Appl. No.: 403,806

[22] PCT Filed: Jul. 30, 1993

[86] PCT No.: PCT/EP93/02042

§ 371 Date: Mar. 16, 1995

§ 102(e) Date: Mar. 16, 1995

[87] PCT Pub. No.: WO94/06929

PCT Pub. Date: Mar. 31, 1994

[30] Foreign Application Priority Data

Sep. 17, 1992 [DE] Germany ........................ 42 31 066.0
May 5, 1993 [DE] Germany ........................ 43 14 870.0

[51] Int. Cl.$^6$ .................... G01N 33/574; C07K 16/00
[52] U.S. Cl. ................ 435/7.23; 435/344; 435/344.1; 436/64; 436/813; 530/388.8; 530/387.7; 530/391.3; 530/387.3; 424/155.1; 424/174.1; 424/178.1
[58] Field of Search ..................... 530/388.2, 388.8, 530/387.7, 391.3; 424/9, 155.1, 174.1, 178.1; 435/240.27, 7.2, 7.23; 436/64, 813

[56] References Cited

FOREIGN PATENT DOCUMENTS 0323802  12/1988  European Pat. Off. .
0356397  8/1989   European Pat. Off. .
0443599  2/1991   European Pat. Off. .

OTHER PUBLICATIONS

Waibel et al (1993) Cancer Res. 53:2840–2845.
Stahel et al (1985) Int. J. Cancer 35:11–17.
Smith et al (1989) Brit. J. Cancer 59(2):174–78.
Ogasawara et al (1988) Cancer Res. 48:412–417.
Waibel et al (1988) Cancer Res. 48:4318–4323.
Kibbelaar et al (1989) J. Pathol. 159:23–28.
Lynch (1993) Chest 103:436S–39S.
Kibbelaar et al (1991) Eur. J. Cancer 27(4) 431–435.
Moolenaar et al (1990) Cancer Res 50:1102–1106.

*Primary Examiner*—Toni R. Scheiner
*Attorney, Agent, or Firm*—Millen, White, Zelano & Branigan, P.C.

[57] ABSTRACT

The invention relates to a novel epitope of 180,000 daltons for the NCAM antigen and a monoclonal antibody, SEN7, directed against this antigen, and their use in diagnosis and therapy of small-cell carcinoma of the lung. The antibody SEN7 reacts significantly more selectively than previously known antibodies with cells of small-cell carcinoma of the lung, and binds with high avidity. In particular, no reaction occurs with leucocytes or healthy kidney or lung epithelial cells. The novel antigen is dominantly expressed by cells of small-cell carcinoma of the lung with a high copy number.

10 Claims, No Drawings

TUMOR-SPECIFIC ANTIBODIES AND ANTIGEN

DESCRIPTION

The invention relates to a novel tumour antigen and antibodies directed against this antigen, and to their use in diagnosis and therapy of small-cell carcinoma of the lung.

Small-cell carcinoma of the lung is prone to premature metastasis formation. Because of this, a surgical, radiological or chemotherapeutic treatment leads, in a large number of cases, only to a temporary cure. In regressions, therapy resistance against previously effective therapies, such as, for example, irradiation and chemotherapy, occur as a complication. Because of this, it has been considered in future to subject the patient after the conventional treatment of the primary tumour to a specific aftertreatment with antibodies or antibody-conjugated active substances. Labelled antibodies would also be useful for the demonstration of metastases by means of imaging processes or for the examination of tumour tissue by means of histological techniques.

A number of antigens which are expressed by cells of small-cell carcinoma of the lung are known; in accordance with the agreement which has been reached in specialist congresses (First and Second International Workshop on Lung Cancer Antigens; Brit.J. Cancer (1991) 63 (suppl.), pages 10–19; J. Nat Cancer Inst. (1991) 83, 609–612), these are divided into seven groups. Antibodies against these antigens are also known. In animal models, these antibodies have occasionally been employed for the localisation of tumour cells. Important previously known antigens of small-cell carcinoma of the lung are the adhesion molecule of neuronal cells (neural cell adhesion molecule; NCAM), and antigens of the clusters 2 and w4. Further antigens are mucins, the Lewis$^y$ antigen, and the antigens of the ABO blood group system. Antibodies against NCAM and against cluster w4 antigens also bind to leucocytes. Antibodies against cluster 2 antigens also bind to epithelial tissue. Because of this, antibodies of this type are not suitable for systemic applications, as would be desirable for an immunological tumour therapy. A high avidity to the particular antigen is additionally useful so that the antibody is strongly concentrated in the tumour tissue.

Antigens discovered to date having a relative specificity for cells of small-cell carcinoma of the lung and antibodies which are directed against these antigens are not sufficiently selective. They do not permit the reliable detection of cells of small-cell carcinoma of the lung. For methods for the immunological treatment of this disease, the specificity of previously known tumour antigens and avidity of the previously known antibodies are also inadequate. The object of the invention is to provide novel tumour antigens of small-cell carcinoma of the lung, as well as antibodies against these antigens, in order to improve diagnosis and therapy of this cancer. In detail, the object is to provide improved antigens which are dominantly expressed if possible exclusively in tumours in high copy number. Antibodies against antigens of this type should be distinguished by a high avidity.

A novel antigen on the cell surface of cells of small-cell carcinoma of the lung has now been found and characterised which is significantly more specific than previously known antigens for tumour cells, and which in particular does not occur on leucocytes or healthy kidney or lung epithelial cells. The novel antigen is dominantly expressed with a high copy number by cells of small-cell carcinoma of the lung.

According to the invention, a monoclonal antibody is provided which binds to the novel antigen specifically and with high avidity.

The invention consequently relates to a murine monoclonal antibody having the designation SEN7, and also a hybridoma cell line having the designation SEN7.2a.4 and the deposit number DSM ACC 2050, which secretes the monoclonal antibody SEN7.

The invention furthermore relates to humanised antibodies having murine hypervariable domains and human framework and constant domains, characterised in that they contain hypervariable domains from the monoclonal antibody SEN7.

The invention also relates to an antigen, in particular of human origin, from cells of small-cell carcinoma of the lung, characterised in that it is bound by the antibody SEN7.

The invention also relates to antibody conjugates, in particular conjugates with a toxin, a radioisotope and/or a labelling agent, characterised in that, as the antibody component, they contain the antibody SEN7 or a humanised antibody having the hypervariable domain of the antibody SEN7.

The invention furthermore relates to the use of the antibody SEN7 or a humanised antibody having the hypervariable domain of the antibody SEN7 and/or of an antibody conjugate which, as the antibody component, contains the antibody SEN7 or a humanised antibody having the hypervariable domain of the antibody SEN7, for the production of a preparation for the treatment and/or diagnosis of small-cell carcinoma of the lung.

The invention furthermore relates to the use of the antibody SEN7 or of a humanised antibody having the hypervariable domain of the antibody SEN7 and/or of an antibody conjugate which, as the antibody component, contains the antibody SEN7 or a humanised antibody having the hypervariable domain of the antibody SEN7, for the treatment and/or diagnosis of small-cell carcinoma of the lung.

Customarily, monoclonal antibodies are obtained from rodent cells, in particular from cells of mice. These antibodies produce undesired immune reactions on in-vivo use in humans. In order to avoid these undesired immune reactions, antibodies which are intended for in-vivo use in humans are modified such that the human immune system no longer recognises these as foreign. The modification processes customary for these purposes include CDR grafting (Jones, P. T. et al. (1986) Nature 321, 14–17; Kettleborough, C. A. et al. (1991) Protein Engineering 4, 773–783). Further possible modification processes are known to the person skilled in the art. Modified antibodies of this type are designated according to the invention as humanised antibodies.

In order to allow the analytical detection of antibodies, these are linked to labelling agents (tracers). For example, antibodies can be labelled with radioisotopes: radioisotopes of yttrium, of rhenium and of technetium and in particular I 125 and I 131, and also In 111 are customary for these purposes. The processes for isotopic labelling and additional radioisotopes suitable for labelling are known to the person skilled in the art. Besides these radio labelling agents, further non-isotopic labelling agents are familiar to the person skilled in the art. These are often preferred in analytical tasks. Labelling is possible, for example, with fluorescent substances, such as, for example, fluorescein, or alternatively with enzymes, such as, for example, peroxidase or alkaline phosphatase. The selection of suitable fluorescent substances or of enzymes and the necessary detection methods are known to the person skilled in the art. In many cases it is useful not to link the labelling agent directly to the antibody, but indirectly by means of additional strongly binding ligands. The combinations biotin/avidin or biotin/streptavidin, in particular, have proven suitable for this purpose.

The selection of ligands of this type and the necessary binding processes are known to the person skilled in the art. According to the invention, corresponding to these examples the term labelling agent is to be understood as meaning both the labelling agents used in direct labelling processes and the combinations used in indirectly labelling processes including the binding ligands.

In some immunological therapy processes, the biological action of the antibodies is utilised directly. In other immunological therapy processes compounds are additionally or even exclusively employed which are intended to damage the diseased tissue. This damage can be effected, for example, by radioactively emitting isotopes such as, for example, I 131 or I 125 or by cytotoxic substances, which include vegetable or bacterial toxins and cytostatics, such as, for example, ricin A, or gelonin. Further suitable radioactive isotopes and further suitable cytotoxic substances are known to the person skilled in the art. All these substances are combined according to the invention under the term toxins. The antibody transports the toxin to the intended site of action, for example the tumour, where it destroys the diseased cells.

Mice were immunised for the experiments which led to the provision of the antigen according to the invention and of the antibodies directed against this antigen. The immunogen used were cells of small-cell carcinoma of the lung which had previously been treated with neuraminidase. Cells of the human cell line SW2 were used in particular for this purpose. During the investigation of the resulting murine monoclonal antibodies, a cell line was discovered which secreted an antibody of the isotype IgG1, which was named SEN7. This antibody reacted with all small-cell carcinoma of the lung cell lines investigated (15). No reaction was observed with cell lines of pavement cell carcinoma of the lung (3) and of adenocarcinoma of the lung (3). It emerged that this antibody is specific for a previously unknown epitope of the neuronal cell adhesion molecule (NCAM), which belongs to none of the previously known groups. The cell line which secretes the antibody SEN7 is deposited in the German collection for microorganisms and cell cultures (Brunswick, Del.) under the description SEN7.2a.4 (deposit number DSM ACC 2050).

The characterisation of the novel epitope of the NCAM molecule, which is recognised by the monoclonal antibody SEN7, is described in the following. The antibody SEN7 is also characterised. Further experimental details are found in the examples. The standard biochemical methods for antibody production and isolation, for characterisation of antibody and antigen and for derivatisation with radioactive isotopes are known to the person skilled in the art and are described in reference books and review articles, for example in Antibodies, a Laboratory Manual (Harlow and Lane (eds) (1988), Cold Spring Harbor Laboratory). Customary process variants are also described therein.

For the immunisation of mice (BALB/c), cells of small-cell carcinoma of the lung (cell line SW2) were treated with neuraminidase. Details of processes of this type and suitable immunisation schemes are known to the person skilled in the art from the literature, for example from Int. J. Cancer 35, 11–17 (1985) and Cancer Research 48, 412–417 (1988). The cell line P3X63Ag8.653 was used as a fusion partner.

The fused cells were cultured and cloned and the clones were cultured again. The antibodies produced were examined by means of indirect immunofluorescence for the binding of untreated and neuraminidase-treated SW2 cells. Cell lines were furthermore selected whose antibodies did not react with cells from bone marrow or with leucocytes. The binding of the antibody to the cells can be detected here with the aid of fluorescently labelled secondary antibodies.

The antibody SEN7 isolated in this way was typed and emerged as belonging to the IgG1 isotype.

Cells which produce SEN7 were cultured in a hollow fibre system. The antibodies were purified from the culture filtrate by affinity chromatography on a protein A column.

A Western blot analysis was carried out in order to characterise the antigen which is recognised by the antibody SEN7. The cell line OH3 which originates from small-cell carcinoma of the lung, and which reacts with the antibody SEN7, is used as the source of the antigen. Surface antigens of the cells were in each case extracted by detergent treatment in the presence of a mixture of various protease inhibitors. The extracts were separated by electrophoresis on polyacrylamide gel in the presence of sodium dodecylsulphate according to a known method. The fractions separated in this way did not react with the antibody SEN7. Because of this, the separated fractions were first renatured with urea according to known methods. A conspicuous protein band having a molecular weight of 180,000 daltons was visible after this treatment. This band was present in the case of the cell lines SW2 and OH3 under non-reducing conditions; it was absent in the negative control without first antibody.

To characterise the antigen further, SW2 cells were cultured in the presence of tunicamycin. In this process, the biosynthesis of nitrogen-bound carbohydrates is inhibited. FACScan analysis of cultured cells of this type showed that they did not react with the antibody SEN7. The epitope to which the antibody SEN7 binds consequently contains an asparagine-bound oligosaccharide. The antigen is consequently a glycoprotein.

To characterise the antibody, serial dilutions of SW2 cells were treated with isotopically labelled antibody. The free and the cell-bound content of the antibody was then determined by measurement of the radioactivity. The analysis of the data showed that the antibody binds with an affinity constant $K_a = 2 \times 10^9 M^{-1}$, and that about 200,000 binding sites per cell are present.

In order to determine the binding specificity of the antibody SEN7, investigations were carried out on viable cells of various carcinoma cell lines by means of indirect immunofluoresence. All 16 cell lines of small-cell carcinoma of the lung which were investigated reacted positively. No staining was observed in three investigated cell lines (U1752, HOTZ and LX1; squamous cell carcinoma, or undifferentiated carcinoma of the lung). The same applies to three further investigated cell lines (A125, SLC52 and A549; adenocarcinomas).

Investigations of leucocytes and peripheral blood lymphocytes demonstrated that the antibody does not bind to these cells. In further investigations it was also established by means of haemagglutination that no binding to erythrocytes takes place. In contrast to known antibodies to antigen groups cluster-1 and cluster-w4, which react non-selectively with leucocytes and lymphocytes, the antibody according to the invention does not react with these cells. The epitope of NCAM according to the invention is thus not present on the surface of these cells.

Tissue samples of tumours and of healthy tissue were further investigated by means of the known immunoperoxidase staining: small-cell carcinoma of the lung, or carcinoid, reacted positively (six out of seven, or two out of three samples respectively). All other tumour tissues investigated (adenocarcinoma, breast cancer, colonic cancer, renal carcinoma and lymphoma) gave no reaction. Individual cell types reacted positively in healthy thyroid gland, adrenal gland, muscle, testicle, peripheral nerve, spinal cord, brain and pituitary gland tissue. The reaction with healthy tissues from skin, bronchi, lung, kidney, liver, large intestine, lymph nodes and pancreas was completely negative.

The distribution of the antibody was determined in xenograft-bearing mice as a model system for imaging processes and for therapeutic use. For this purpose, $10^7$ washed cells of the cell line SW2 were in each case injected subcutaneously into mice. The investigations were started as soon as the tumours had reached an approximate weight of 100 mg. At this point in time, a mixture of equal parts of SEN7 antibody ($^{125}$I-labelled) and, as a control, MG-1 antibody ($^{131}$I-labelled) was injected into the animals. Like the antibody SEN7, the control antibody belongs to the class IgG1. The organ distribution of the two antibodies was determined over a period of several days. The antibody was absorbed into the tumour from the blood circulation: after the third day a three- to five-fold higher concentration of antibody SEN7 was measured in the tumour than in the blood. This absorption was specific: compared with the concentration in the tumour, the concentration in the liver (site of non-specific degradation reactions) was between fifteen and twenty five times smaller. The amount of the injected dose, relative to the fresh weight of the organ, was at most 32%.

Without further elaboration, it is believed that one skilled in the art can, using the preceding description, utilize the present invention to its fullest extent. The preferred specific embodiments are, therefore, to construed as merely illustrative, and not limitative of the disclosure in any way whatsoever.

The entire disclosures of all applications, patents, and publications cited above and below, and of corresponding applications German DE 42 31 066, filed Sep. 17, 1992, and DE 43 14 870, filed May 05, 1993, are hereby incorporated by reference.

EXAMPLES

The following abbreviations are used:

PBS: phosphate-buffered saline solution (137 mM NaCl, 2.7 mM KCl, 8 mM $Na_2HPO_4$, 1.5 mM $KH_2PO_4$)
BSA: bovine serum albumin
TCA: trichloroacetic acid
DMSO: dimethyl sulphoxide
DMF: dimethylformamide
TBS buffer: TRIS buffer (50 mM; pH 7.3) containing 1M NaCl For the culture of the hybridoma cell lines, if nothing else is described, a medium based on RPMI 1640 medium having the following additives is used: 10% (v/v) foetal calf serum, 10% (v/v) supplement H1 (BM-Condimed®, Boehringer Mannheim), 1% (v/v) L-glutamine, and 1% (v/v) of an insulin-oxalacetate-pyruvate solution (1.5 mg of cis-oxalacetic acid, 0.5 g of sodium pyruvate and 2000 units of insulin are added to 80 ml of $H_2O$; then HCl is added until the solution is clear (pH 3–4) and the solution is made up to 100 ml with $H_2O$).

Incubations, if not stated otherwise, are carded out at room temperature (R.T.; 15°–28° C.).

Example 1

Preparation of the Hybridoma Cell Line SEN7.2a.4, Which Secretes the Antibody SEN7

The immunisation of mice (BALB/c) is carried out by the process of Stahel, R. A. et al. (1985) Int. J. Cancer 35, 11–17. Cells of small-cell carcinoma of the lung (cell line SW2; Dana Farber Institute, Boston/Mass./USA) are treated with neuraminidase from Clostridium perfringens (2 hours at 37° C.; 1 enzyme unit of neuraminidase/$10^6$ cells).

After the immunisation, the method is further performed as described in the publication cited above. Cells of the cell line P3X63-Ag8.653 are used as fusion partners.

The fused cells are cultured and cloned and the clones are cultured again. The antibodies produced are examined by means of indirect immunofluorescence for the binding of untreated and neuraminidase-treated SW2 cells. Cell lines are selected whose antibodies do not react with cells from bone marrow or with leucocytes. For the immunofluorescence examination, $2 \times 10^5$ cells (tumour, bone marrow or blood cells) are in each case aliquoted into a test tube and incubated at 4° C. for one hour with $10^{-7}$M of the antibody to be investigated in 25 µl of PBS with the addition of 0.1% sodium azide. The cells are washed and treated with 50 µl of a solution which contains fluorescein-labelled anti-mouse antibody (goat) and washed again. The binding of the antibody to the cells can be detected by means of the fluorescence.

The antibody isolated in this way is named SEN7. It belongs to the isotype IgG1/kappa, as investigations using test sticks (Amersham, GB) show.

Example 2

Production and Purification of the Antibody SEN7

Cells of the cell line SEN7.2a.4 are cultured in a hollow fibre system (Acusyst, Technomara, CH) in RPMI 1640 medium with the addition of 10% by volume of foetal calf serum and 2 mM L-glutamine. The antibodies are adsorbed from the culture filtrate on a protein A column (BIO-RAD, Richmond/Calif., USA). To do this, the culture filtrate is applied to the column in 50 mM Tris-HCl (pH 8.9) containing 3.3M NaCl and the column is then washed with 50 mM Tris-HCl (pH 8.9) containing 3.3M NaCl until the eluate is protein-free. The bound IgG antibodies are eluted with 50 mM sodium acetate buffer (pH 6.0) containing 150 mM NaCl. The eluate is dialysed against 25 mM sodium acetate buffer (pH 5.5) and applied to an ion exchange column (Mono-S®, Pharmacia, Uppsala, SE) and eluted using an NaCl gradient.

The antibody preparation obtained in this way proves to be homogeneous on investigation by means of SDS-PAGE and isoelectric focusing.

Example 3

Isotopic Labelling of the Antibody SEN7

For labelling with $^{125}$I, 40 µg of IodoGen® (Pierce, UK) are dissolved in 50 µl of chloroform. The solution is concentrated to dryness in a 1.5 ml vessel. A solution of 100 µg of SEN7 antibody in 50 µl of PBS, and a solution which contains 200 µCi of a $^{125}$I iodide salt are added to this vessel.

The reaction mixture is stirred for five minutes.

The reaction is then stopped by addition of 50 μl of a saturated solution of tyrosine (Fluka) in PBS. A column packed with SEPHADEX® G-25 is equilibrated with a solution of BSA (10 g/l) in PBS and used for the separation of the iodine which was not bound to protein.

The radiochemical purity of the labelled protein is determined by means of TCA precipitation and is greater than 95%.

The iodine isotope $^{131}$I is introduced in an analogous manner. The same reaction is also used in order to prepare isotopically labelled derivatives of other antibodies (e.g. MG-1).

Example 4

Western Blot Analysis of the SEN7 Antigen

A Western blot analysis is carded out in order to isolate the antigen which is recognised by the antibody SEN7. The cell line OH3, which originates from small-cell carcinoma of the lung, and which reacts with the antibody SEN7, is used as a source of the antigen.

$10^7$ cells are extracted for one hour at 0° C. in PBS with the addition of 45 mM 3-[(3-cholamidopropyl)dimethylammonio]propanesulphonate (CHAPS) and 0.1% NaN$_3$, and a mixture of various protease inhibitors (0.1 mM 1,10-phenanthroline, 0.1 mM 3,4-dichloroisocoumarin, 0.05 mM N-[N-(L-3-trans-carboxiran-2-carbonyl)-L-leucyl]agmatine (E-64), 50 μg/ml of pepstatin A and 0.1 mg/ml of Calpain inhibitor peptide).

To do this, the suspensions are briefly mixed by means of a vortex mixer. The extract is then removed from the cell debris by centrifugation (1h; 100 000×g). The extracts are separated by electrophoresis on polyacrylamide gel (7.5%) in the buffer system of O'Farrel in the presence of sodium dodecylsulphate. The gels are in each case renatured for 30 minutes in 6M, 3M and 1.5M urea, then in water and in transfer buffer (pH 10.5; 10 mM 3-[cyclohexylamino]-1-propanesulphonic acid, 10% methanol). The proteins are then transferred by electrophoresis to an Immun-Lite P membrane (BioRGG, CH) with 100 Vh. The membrane is pretreated, as described by Johnson, D. A. et al. (1984) Gene Anal. Tech., 1, 328–334, with 50 g/l of skimmed milk powder in PBS and then incubated overnight at 4° C. with affinity-purified SEN7 having a concentration of $10^{-7}$M. Unbound antibody is washed out with a solution of 0.5 g/l of TWEEN 20 in PBS. The gels are treated with a solution of goat anti-mouse IgG, which is conjugated with alkaline phosphatase. After washing, the bands are rendered visible by incubation with a light-emitting substrate on X-ray film.

A single protein band having a molecular weight of 180,000 is observed. In the case of the cell line OH3 this band is present under non-reducing conditions; it is missing in the negative control without the first antibody.

Example 5

Determination of the Binding Constants of SEN7

A serial dilution of SW2 cells in 100 μl of PBS with the addition of 1% bovine serum albumin and 0.1% sodium azide, starting with $10^7$ cells, is prepared. Each dilution is treated for two hours at 4° C. with 40 ng of isotopically labelled antibody according to Example 3. The cells are then centrifuged off and the free and the cell-bound amount of the antibody are determined by measurement of the radioactivity.

The analysis of the data establishes that the antibody binds with an affinity constant $K_a = 2 \times 10^9 M^{-1}$, and that about 200,000 binding sites per cell are present.

Example 6

Reaction of Antibody SEN7 With NCAM-Transfected Cells

The reaction of the antibody SEN7 was investigated in cells which had been transfected with a complementary DNA. This cDNA codes for a 140,000 daltons isoform of a human NCAM (neuronal cell adhesion molecule) from the small-cell bronchial carcinoma cell line SW2. These stable transfectants were prepared as follows.

The coding region for the 140,000 daltons isoform of NCAM was cloned from cDNA by means of the PCR method (polymerase chain reaction). The polyA+RNA, from which the cDNA was synthesised, originated from the human small-cell bronchial carcinoma cell line SW2. Three overlapping DNA fragments were prepared and each was then cloned and sequenced in pSK+Bluescript (Stratagene GMBH, Zurich). Fragment 1 was cut by means of restriction enzymes (EcoRI/NotI) and the cut piece was isolated. Fragment 2 was cut using EcoRI/BstBI and isolated; fragment 3 was cut using BstBI/NotI and isolated. These three cut fragments were joined again and gave the coding sequence of the human 140,000 daltons NCAM. This clone was then subcloned in the eukaryotic expression vector pRC/CMV (Invitrogen, Heidelberg) by means of HindIII/NotI restriction enzymes.

Transfection into a mouse pre-B cell line B-300.19 (Reth et al., 1986, Nature 322: 840–842) was carried out by means of electroporation. To do this, 40 ng of uncut plasmid were inserted in $10^7$ mouse cells. The cells were then selected for geneticin resistance; the vector used contains a geneticin resistance gene. The resistant clones were investigated for surface expression of NCAM. A clone having particularly high and uniform expression of NCAM was selected.

This clone was positive with the antibody SEN7 and other known anti-NCAM antibodies. This clone was negative with an anti-cluster-w4/CD24 antibody SWA11.

Example 7

Competition of Antibody SEN7 and Other NCAM Antibodies

NCAM antibodies, which recognise three different epitopes on small-cell bronchial carcinomas (Moolenaar, C.E.C.K. et al., Cancer Res. 50: 1102–1106, 1990; Hida, T. et al., Br. J. Cancer, 63: Suppl. XIV, 24–28, 1991), were investigated for their action blocking SEN7 binding to bronchial carcinoma cells. In a radioimmunoexperiment, $10^5$ cells were first treated with an excess of competing first NCAM antibodies.

The cells were then incubated with $^{125}$I-labelled antibody SEN7 (using half saturation concentration). Unbound antibody was washed out and the still bound radioactivity was determined. As can be seen from the following table 1, no or only slight competition of the other antibodies with SEN7 for binding to tumour cells was found.

TABLE 1

Binding competition in small-cell bronchial carcinoma cells between the radiolabelled SEN7 antibody and non-labelled antibodies against NCAM[a]

| Non-labelled antibodies | SAM (cpm)[b] | % Binding |
|---|---|---|
| none | (138) | 100 |
| SEN7 | (1588) | 1 |
| first editope | | |
| 123C3 | (1469) | 39 |
| 123A8 | (1967) | 55 |
| NCC-Lu-234 | (1994) | 74 |
| NKI-nbl-3 | (2352) | 87 |
| SEN36 | (1656) | 126 |
| second epitope | | |
| MOC-21 | (2214) | 68 |
| NCC-LU-246 | (1644) | 78 |
| NE25 | (1447) | 85 |
| MOC-1 | (1668) | 103 |
| third epitope | | |
| NKH 1 | (2282) | 33 |
| Leu 19 | (1138) | 99 |

[a] Proportion of binding of SEN7 in %
[b] Bound first (competing) antibody was quantified by means of $^{125}$I-labelled sheep anti-mouse antibody.

Example 8

Immunoperoxidase Staining of Tissues

Tissue samples of tumours and of healthy tissue are examined by means of immunoperoxidase staining: frozen sections (thickness 5 μm) are prepared and mounted on a slide coated with glue. After a pretreatment with 0.3% (v/v) $H_2O_2$ in methanol and with pig serum (2%), the sections are covered with a solution of SEN7 and incubated at room temperature for one hour. The sections are then washed and first treated with peroxidase-conjugated anti-mouse rabbit serum, then with peroxidase-conjugated anti-rabbit pig serum. The peroxidase is rendered visible using 3,3'-diaminobenzidine as the chromogenic substrate. The sections are counterstained with haematoxylin. The results are summarised in the following table 2:

TABLE 2

| Tissue | Reaction |
|---|---|
| (Number of samples) | |
| Small-cell carcinoma of | |
| the lung (7) | positive (6 of 7) |
| Carcinoid (3) | positive (2 of 3) |
| Adenocarcinoma (3) | negative |
| Carcinoma of the breast (4) | negative |
| Colonic carcinoma (4) | negative |
| Renal carcinoma (4) | negative |
| Lymphoma (1) | negative |
| Skin (3) | negative |
| Bronchi (4) | negative |
| Lung (3) | negative |
| Kidney (4) | negative |
| Liver (3) | negative |
| Lymph nodes (3) | negative |
| Pancreas | negative |
| Thyroid gland (5) | positive (follicle cells) |
| Adrenal glands (3) | positive (Zona glomerulosa and medulla) |
| Skeletal muscle (3) | |
| Testicles (1) | positive (individual fibres) |
| Peripheral nerves (4) | positive (Leydig's cells) |
| | positive (axons) |

TABLE 2-continued

| Tissue | Reaction |
|---|---|
| Bone marrow (3) | positive |
| Brain (3) | positive (neuropil) |
| Pituitary gland (2) | positive (cells of the posterior lobe and individual cells of the anterior lobe) |

Example 9

Xenograft Investigation in Mice

Preparation: $10^7$ washed cells of the cell line SW2 are in each case injected subcutaneously into female ICR nu/nu mice (4–6 weeks old) which are fed under pathogen-free conditions. The investigations are started as soon as the tumours have reached an approximate weight of 100 mg (about two to three weeks after the injection).

Procedure: A mixture of equal parts of SEN7 antibody (6 μg/animal; $^{125}$I-labelled using 12 μCi) and, as the control, MG-1 antibody (6 μg/animal; $^{131}$I-labelled using 12 μCi) is injected i.v. into the animals. Like the antibody SEN7, the control antibody belongs to the class IgG1.

Four mice in each case are sacrificed after 2, 4 and 7 days and the various organs are washed with PBS and weighed. The two antibodies are measured using a two channel gamma counter (15–80 keV and 260–470 keV). The results are summarised in the following table 3:

TABLE 3

| | Day | | |
|---|---|---|---|
| | 2 | 4 | 7 |
| Quotient tumour/blood | 1.9 | 3.2 | 5.6 |
| Quotient tumour/liver | 8.0 | 15.9 | 25.3 |
| % injected dose/g of organ[a] | | | |
| Organ: | | | |
| Tumour | 19.3 ± 5.0 | 33.4±10.3 | 10.1±4.3 |
| Blood | 10.2 ± 1.5 | 10.3±2.8 | 1.8±0.7 |
| Liver | 2.4 ± 0.3 | 2.1±0.9 | 0.4±0.1 |
| Heart | 1.0 ± 0.2 | 0.9±0.4 | 0.2±0.1 |
| Lung | 2.2 ± 0.4 | 1.4±0.4 | 0.5±0.3 |
| Kidney | 1.4 ± 0.4 | 1.2±0.6 | 0.2±0.0 |
| Spleen | 1.6 ± 0.3 | 1.4±0.5 | 0.3±0.1 |
| Muscle | 0.6 ± 0.1 | 0.6±0.1 | 0.1±0.0 |
| Brain | 0.1 ± 0.0 | 0.1±0.0 | 0.0±0.0 |
| Bone | 0.8 ± 0.2 | 0.5±0.1 | 0.1±0.0 |

[a] Mean value ± standard deviation (n = 3 or 4)

I claim:

1. A murine monoclonal antibody SEN7, which antibody is secreted by hybridoma SEN.7.2a.4, DSM ACC 2050.

2. A hybridoma cell line SEN7.2a.4, deposit number DSM ACC 2050, which secretes the monoclonal antibody according to claim 1.

3. Humanised antibody having murine hypervariable domains and human framework and constant domains, characterised in that it contains hypervariable domains from the monoclonal antibody according to claim 1.

4. An antibody conjugate, comprising an antibody of claim 1 as the antibody component.

5. A method of diagnosing a small-cell carcinoma of the lung, comprising contacting a sample containing antigens with an antibody according to claim 1, and detecting the amount of antibody bound to an antigen of a small-cell carcinoma in said sample.

6. A method of claim 5, wherein said sample comprises cells or a tissue extract.

7. A method of diagnosing a small-cell carcinoma of the lung, comprising contacting a sample containing antigens with an antibody according to claim 4, and detecting the amount of antibody bound to an antigen of a small-cell carcinoma in said sample.

8. A method of claim 4, wherein said sample comprises cells or a tissue extract.

9. A method of treating a small-cell carcinoma of the lung, comprising administering an effective amount of antibody of claim 4.

10. An antibody conjugate of claim 4, wherein the antibody component is conjugated to a detectable label.

* * * * *